US012685602B2

(12) United States Patent
Hoelzle et al.

(10) Patent No.: US 12,685,602 B2
(45) Date of Patent: Jul. 21, 2026

(54) ROBOTICALLY-ASSISTED COCHLEAR IMPLANT SYSTEM

(71) Applicants: Ohio State Innovation Foundation, Columbus, OH (US); RESEARCH INSTITUTE AT NATIONWIDE CHILDREN'S HOSPITAL, Columbus, OH (US)

(72) Inventors: David Hoelzle, Bexley, OH (US); Oliver F. Adunka, Columbus, OH (US); Gregory Wiet, Columbus, OH (US)

(73) Assignees: Ohio State Innovation Foundation, Columbus, OH (US); RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 290 days.

(21) Appl. No.: 18/282,418

(22) PCT Filed: Mar. 15, 2022

(86) PCT No.: PCT/US2022/020372
§ 371 (c)(1),
(2) Date: Sep. 15, 2023

(87) PCT Pub. No.: WO2022/197694
PCT Pub. Date: Sep. 22, 2022

(65) Prior Publication Data
US 2024/0164858 A1      May 23, 2024

Related U.S. Application Data

(60) Provisional application No. 63/161,086, filed on Mar. 15, 2021.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/75* (2016.02); *A61B 90/06* (2016.02);
(Continued)

(58) Field of Classification Search
None
See application file for complete search history.

(56) References Cited

U.S. PATENT DOCUMENTS 8,620,473 B2    12/2013  Diolaiti et al.
9,333,042 B2 *   5/2016  Diolaiti .............. A61B 1/00087
(Continued)

FOREIGN PATENT DOCUMENTS

WO          2011143338 A1    11/2011

OTHER PUBLICATIONS

International Searching Authority (ISA/US). International Search Report and Written Opinion. Issued in PCT Application No. PCT/US2022/020372 on Jun. 2, 2022. 9 pages.
(Continued)

*Primary Examiner* — Carl H Layno
*Assistant Examiner* — Bryan Mcallister Lee
(74) *Attorney, Agent, or Firm* — Meunier Carlin & Curfman LLC

(57)          ABSTRACT

A robotic system for cochlear implantation (CI) is described herein. The system includes a robotic tool configured to hold a cochlear implant electrode array and a controller that is operably coupled to the robotic tool. The controller includes a processor and a memory. The memory has computer-executable instructions stored thereon that, when executed
(Continued)

by the processor, cause the processor to control the robotic tool with the degrees of freedom of a human hand.

19 Claims, 5 Drawing Sheets

(51) Int. Cl.
    *A61B 34/30*          (2016.01)
    *A61B 90/00*          (2016.01)
(52) U.S. Cl.
    CPC ... *A61B 2034/301* (2016.02); *A61B 2034/305* (2016.02); *A61B 2090/064* (2016.02)

(56)                References Cited

U.S. PATENT DOCUMENTS

2007/0088335 A1*   4/2007  Jolly ................... A61N 1/0541
                                                              604/891.1
2017/0086929 A1    3/2017  Moll et al.

OTHER PUBLICATIONS

Amieva H, Ouvrard C, Giulioli C, Meillon C, Rullier L, Dartigues J-F. Self-Reported Hearing Loss, Hearing Aids, and Cognitive Decline in Elderly Adults: A 25-Year Study. J Am Geriatr Soc 2015;63:2099-104. https://doi.org/10.1111/jgs.13649.

Pacala JT, Yueh B. Hearing Deficits in the Older Patient: "I Didn't Notice Anything". JAMA 2012;307:1185. https://doi.org/10.1001/jama.2012.305.

Borda MG, Reyes-Ortiz CA, Heredia RA, Castellanos-Perilla N, Ayala Copete AM, Soennesyn H, et al. Association between self-reported hearing impairment, use of a hearing aid and performance of instrumental activities of daily living. Arch Gerontol Geriatr 2019;83:101-5. https://doi.org/10.1016/j.archger.2019.04.001.

Tsimpida D, Kontopantelis E, Ashcroft D, Panagioti M. Socioeconomic and lifestyle factors associated with hearing loss in older adults: a cross-sectional study of the English Longitudinal Study of Ageing (ELSA). BMJ Open 2019;9:e031030. https://doi.org/10.1136/bmjopen-2019-031030.

Gstoettner W, Kiefer J, Baumgartner W-D, Pok S, Peters S, Adunka O. Hearing preservation in cochlear implantation for electric acoustic stimulation. Acta Otolaryngol (Stockh) 2004;124:348-52. https://doi.org/10.1080/00016480410016432.

James C, Albegger K, Battmer R, Burdo S, Deggouj N, Deguine O, et al. Preservation of residual hearing with cochlear implantation: How and why. Acta Otolaryngol (Stockh) 2005;125:481-91. https://doi.org/10.1080/00016480510026197.

Wolfgang Karl Gstoettner, Oliver Ad. Perimodiolar Electrodes in Cochlear Implant Surgery. Acta Otolaryngol (Stockh) 2001;121:216-9. https://doi.org/10.1080/000164801300043569.

Adunka O, Kiefer J, Unkelbach MH, Lehnert T, Gstoettner W. Development and evaluation of an improved cochlear implant electrode design for electric acoustic stimulation. The Laryngoscope 2004;114:1237-41. https://doi.org/10.1097/00005537-200407000-00018.

Wardrop P, Whinney D, Rebscher SJ, Roland JT, Luxford W, Leake PA. A temporal bone study of insertion trauma and intracochlear position of cochlear implant electrodes. I: Comparison of Nucleus banded and Nucleus ContourTM electrodes. Hear Res 2005;203:54-67. https://doi.org/10.1016/j.heares.2004.11.006.

Dalbert A, Sim JH, Gerig R, Pfiffner F, Roosli C, Huber A. Correlation of Electrophysiological Properties and Hearing Preservation in Cochlear Implant Patients: Otol Neurotol 2015;36:1172-80. https://doi.org/10.1097/MAO.0000000000000768.

Campbell L, Kaicer A, Sly D, Iseli C, Wei B, Briggs R, et al. Intraoperative Real-time Cochlear Response Telemetry Predicts Hearing Preservation in Cochlear Implantation: Otol Neurotol 2016:1. https://doi.org/10.1097/MAO.0000000000000972.

Lo J, Bester C, Collins A, Newbold C, Hampson A, Chambers S, et al. Intraoperative force and electrocochleography measurements in an animal model of cochlear implantation. Hear Res 2018;358:50-8. https://doi.org/10.1016/j.heares.2017.11.001.

Lenarz T, Avci E, Gazibegovic D, Salcher R. First Experience With a New Thin Lateral Wall Electrode in Human Temporal Bones: Otol Neurotol 2019;40:872-7. https://doi.org/10.1097/MAO.0000000000002251.

Brown RF, Hullar TE, Cadieux JH, Chole RA. Residual hearing preservation after pediatric cochlear implantation. Otol Neurotol Off Publ Am Otol Soc Am Neurotol Soc Eur Acad Otol Neurotol 2010;31:1221-6. https://doi.org/10.1097/MAO.0b013e3181f0c649.

Gstoettner WK, Helbig S, Maier N, Kiefer J, Radeloff A, Adunka OF. Ipsilateral Electric Acoustic Stimulation of the Auditory System: Results of Long-Term Hearing Preservation. Audiol Neurotol 2006;11:49-56. https://doi.org/10.1159/000095614.

VonIlberg C, Kiefer J, Tillein J, Pfenningdorff T, Hartmann R, Stürzebecher E, et al. Electric-Acoustic Stimulation of the Auditory System. ORL 1999;61:334-40. https://doi.org/10.1159/000027695.

Gantz BJ, Turner CW. Combining acoustic and electrical hearing. The Laryngoscope 2010;113:1726-30. https://doi.org/10.1097/00005537-200310000-00012.

Woodson EA, Reiss LAJ, Turner CW, Gfeller K, Gantz BJ. The Hybrid cochlear implant: a review. Adv Otorhinolaryngol 2010;67:125-34. https://doi.org/10.1159/000262604.

Pillsbury HC, Dillon MT, Buchman CA, Staecker H, Prentiss SM, Ruckenstein MJ, et al. Multicenter US Clinical Trial With an Electric-Acoustic Stimulation (EAS) System in Adults: Final Outcomes. Otol Neurotol 2018;39:299-305. https://doi.org/10.1097/MAO.0000000000001691.

Gstoettner WK, Van de Heyning P, Fitzgerald O'Connor A, Morera C, Sainz M, Vermeire K, et al. Electric acoustic stimulation of the auditory system: results of a multi-centre investigation. Acta Otolaryngol (Stockh) 2008;128:968-75. https://doi.org/10.1080/00016480701805471.

Gantz BJ, Hansen MR, Turner CW, Oleson JJ, Reiss LA, Parkinson AJ. Hybrid 10 Clinical Trial. Audiol Neurotol 2009;14:32-8. https://doi.org/10.1159/000206493.

Gantz BJ, Dunn C, Oleson J, Hansen M, Parkinson A, Turner C. Multicenter clinical trial of the Nucleus Hybrid S8 cochlear implant: Final outcomes: S8 Hybrid Cochlear Implants. The Laryngoscope 2016;126:962-73. https://doi.org/10.1002/lary.25572.

Suhling M-C, Majdani O, Salcher R, Leifholz M, Büchner A, Lesinski-Schiedat A, et al. The Impact of Electrode Array Length on Hearing Preservation in Cochlear Implantation: Otol Neurotol 2016;37:1006-15. https://doi.org/10.1097/MAO.0000000000001110.

Friedmann DR, Peng R, Fang Y, McMenomey SO, Roland JT, Waltzman SB. Effects of loss of residual hearing on speech performance with the CI422 and the Hybrid-L electrode. Cochlear Implants Int 2015;16:277-84. https://doi.org/10.1179/1754762815Y.0000000008.

Carlson ML, Archibald DJ, Gifford RH, Driscoll CL, Beatty CW. Reimplantation with a conventional length electrode following residual hearing loss in four hybrid implant recipients. Cochlear Implants Int 2012;13:148-55. https://doi.org/10.1179/1754762811Y.0000000003.

Carlson ML, O'Connell BP, Lohse CM, Driscoll CL, Sweeney AD. Survey of the American Neurotology Society on Cochlear Implantation: Part 2, Surgical and Device-Related Practice Patterns. Otol Neurotol 2017:1. https://doi.org/10.1097/MAO.0000000000001631.

Harris MS, Riggs WJ, Giardina CK, O'Connell BP, Holder JT, Dwyer RT, et al. Patterns Seen During Electrode Insertion Using Intracochlear Electrocochleography Obtained Directly Through a Cochlear Implant: Otol Neurotol 2017;38:1415-20. https://doi.org/10.1097/MAO.0000000000001559.

Haumann S, Imsiecke M, Bauernfeind G, Büchner A, Helmstaedter V, Lenarz T, et al. Monitoring of the Inner Ear Function During and After Cochlear Implant Insertion Using Electrocochleography. Trends Hear 2019;23:233121651983356. https://doi.org/10.1177/2331216519833567.

Riggs WJ, Dwyer RT, Holder JT, Mattingly JK, Ortmann A, Noble JH, et al. Intracochlear Electrocochleography: Influence of Scalar

(56)        References Cited

OTHER PUBLICATIONS

Position of the Cochlear Implant Electrode on Postinsertion Results. Otol Neurotol 2019;40:e503-10. https://doi.org/10.1097/MAO.0000000000002202.

Skinner MW, Ketten DR, Holden LK, Harding GW, Smith PG, Gates GA, et al. CT-Derived Estimation of Cochlear Morphology and Electrode Array Position in Relation to Word Recognition in Nucleus-22 Recipients. J Assoc Res Otolaryngol 2002;3:332-50. https://doi.org/10.1007/s101620020013.

Rask-Andersen H, Liu W, Erixon E, Kinnefors A, Pfaller K, Schrott-Fischer A, et al. Human Cochlea: Anatomical Characteristics and their Relevance for Cochlear Implantation. Anat Rec Adv Integr Anat Evol Biol 2012;295:1791-811. https://doi.org/10.1002/ar.22599.

Adunka O, Unkelbach MH, Mack MG, Radeloff A, Gstoettner W. Predicting Basal Cochlear Length for Electric-Acoustic Stimulation. Arch Otolaryngol Neck Surg 2005;131:488. https://doi.org/10.1001/archotol.131.6.488.

Choudhury B, Adunka OF, DeMason CE, Ahmad FI, Buchman CA, Fitzpatrick DC. Detection of Intracochlear Damage With Cochlear Implantation in a Gerbil Model of Hearing Loss: Otol Neurotol 2011;32:1370-8. https://doi.org/10.1097/MAO.0b013e31822f09f2.

Lenarz T, Dalkowski K. Cochlear implantation: the Hannover guideline. Tuttlingen: Endo-Press; 2006.

Wiet GJ, Stredney D, Sessanna D, Bryan JA, Welling DB, Schmalbrock P. Virtual Temporal Bone Dissection: An Interactive Surgical Simulator. Otolaryngol Neck Surg 2002;127:79-83. https://doi.org/10.1067/mhn.2002.126588.

Wiet GJ, Stredney D, Kerwin T, Hittle B, Fernandez SA, Abdel-Rasoul M, et al. Virtual temporal bone dissection system: OSU virtual temporal bone system: Development and Testing. The Laryngoscope 2012;122:S1-12. https://doi.org/10.1002/lary.22499.

Hussong A, Rau TS, Ortmaier T, Heimann B, Lenarz T, Majdani O. An automated insertion tool for cochlear implants: another step towards atraumatic cochlear implant surgery. Int J Comput Assist Radiol Surg 2010;5:163-71. https://doi.org/10.1007/s11548-009-0368-0.

Schurzig D, Webster RJ, Dietrich MS, Labadie RF. Force of Cochlear Implant Electrode Insertion Performed by a Robotic Insertion Tool: Comparison of Traditional Versus Advance Off-Stylet Techniques. Otol Neurotol 2010;31:1207-10. https://doi.org/10.1097/MAO.0b013e3181f2ebc3.

Bell B, Stieger C, Gerber N, Arnold A, Nauer C, Hamacher V, et al. A self-developed and constructed robot for minimally invasive cochlear implantation. Acta Otolaryngol (Stockh) 2012;132:355-60. https://doi.org/10.3109/00016489.2011.642813.

Kratchman LB, Blachon GS, Withrow TJ, Balachandran R, Labadie RF, Webster RJ. Design of a Bone—Attached Parallel Robot for Percutaneous Cochlear Implantation. IEEE Trans Biomed Eng 2011;58:2904-10. https://doi.org/10.1109/TBME.2011.2162512.

Klenzner T, Ngan CC, Knapp FB, Knoop H, Kromeier J, Aschendorff A, et al. New strategies for high precision surgery of the temporal bone using a robotic approach for cochlear implantation. Eur Arch Otorhinolaryngol 2009;266:955-60. https://doi.org/10.1007/s00405-008-0825-3.

Labadie RF, Balachandran R, Noble JH, Blachon GS, Mitchell JE, Reda FA, et al. Minimally invasive image-guided cochlear implantation surgery: First report of clinical implementation: Minimally Invasive Image-Guided CI Surgery. The Laryngoscope 2014;124:1915-22. https://doi.org/10.1002/lary.24520.

Simeunovic A, Hoelzle DJ. Coupled Dynamics of Material Delivery and Robotic Manipulator Axes in Endoscopic Additive Manufacturing. Presented at the IEEE American Control Conference, Philadelphia, PA.

Narciso CE, Contento NM, Storey TJ, Hoelzle DJ, Zartman JJ. Release of Applied Mechanical Loading Stimulates Intercellular Calcium Waves in *Drosophila* Wing Discs. Biophys J 2017;113:491-501. https://doi.org/10.1016/j.bpj.2017.05.051.

Adunka O, Kiefer J, Unkelbach MH, Radeloff A, Gstoettner W. Evaluating cochlear implant trauma to the scala vestibuli: Scala vestibuli cochlear implantations. Clin Otolaryngol 2005;30:121-7. https://doi.org/10.1111/j.1365-2273.2004.00935.x.

Choudhury B, Adunka OF, Awan O, Pike JM, Buchman CA, Fitzpatrick DC. Electrophysiologic Consequences of Flexible Electrode Insertions in Gerbils With Noise-Induced Hearing Loss: Otol Neurotol 2014;35:519-25. https://doi.org/10.1097/MAO.0b013e31829bdf2b.

Lakie M, Vernooij CA, Osborne TM, Reynolds RF. The resonant component of human physiological hand tremor is altered by slow voluntary movements. J Physiol 2012;590:2471-83. https://doi.org/10.1113/jphysiol.2011.226449.

Adunka O, Unkelbach MH, MacK M, Hambek M, Gstoettner W, Kiefer J. Cochlear implantation via the round window membrane minimizes trauma to cochlear structures: A histologically controlled insertion study. Acta Otolaryngol (Stockh) 2004;124:807-12. https://doi.org/10.1080/00016480410018179.

Eshraghi AA, Yang NW, Balkany TJ. Comparative study of cochlear damage with three perimodiolar electrode designs. The Laryngoscope 2003;113:415-9. https://doi.org/10.1097/00005537-200303000-00005.

* cited by examiner

ROBOTICALLY-ASSISTED COCHLEAR IMPLANT SYSTEM

CROSS-REFERENCE TO RELATED APPLICATIONS

This application is a United States National Phase Patent Application of International Patent Application Number PCT/US2022/020372, filed on Mar. 15, 2022, which claims the benefit of U.S. provisional patent application No. 63/161,086, filed on Mar. 15, 2021, and titled "ROBOTI-CALLY-ASSISTED COCHLEAR IMPLANT SYSTEM," the disclosure of which are expressly incorporated herein by reference in their entireties.

BACKGROUND

A relatively large proportion of the adult population in the United States has hearing loss. Specifically, nearly 25 percent of adults aged 65 to 74 years of age have disabling hearing loss, a number that further increases with age. While cochlear implantation (CI) has been demonstrated to be highly effective in this population, it is estimated that only about 3-5 percent of adult candidates receive this intervention. While the reasons for the low penetrance of cochlear implantation in the population appear multifactorial, the loss of residual hearing (RH) typically associated with CI appears to be a main deterrent for potential candidates. In particular, the loss of hearing from this procedure has been linked to the insertion of the electrode carrier into the cochlea. Thus, patients fear that hearing with the device may not exceed what their residual natural hearing can provide.

SUMMARY

A robotic system for cochlear implantation (CI) is described herein. The system includes a robotic tool configured to hold a cochlear implant electrode array and a controller that is operably coupled to the robotic tool. The controller includes a processor and a memory. The memory has computer-executable instructions stored thereon that, when executed by the processor, cause the processor to control the robotic tool with the degrees of freedom of a human hand.

Optionally, the degrees of freedom comparable to a human hand include at least one of pitch, roll, or yaw.

Alternatively or additionally, the system optionally includes a sensor operably coupled to the controller. The sensor is configured to detect a surgical procedure quality metric. For example, the sensor can be a force sensor, a pressure sensor, an accelerometer, an inertial sensor, or an electrode. Optionally, the memory has further computer-executable instructions stored thereon that, when executed by the processor, cause the processor to receive a feedback signal from the sensor, and control the robotic tool in response to the feedback signal.

Alternatively or additionally, the robotic tool includes a plurality of kinematic elements. The kinematic elements can include a prismatic joint, a revolute joint, or combinations thereof. The kinematic elements can include one or more kinematic elements configured for gross positioning and rotation, one or more kinematic elements configured for fine rotation, and one or more kinematic elements configured for retracting an end effector of the robotic tool.

Alternatively or additionally, the robotic tool includes an end effector. The end effector is tapered at a distal end.

Alternatively or additionally, the memory has further computer-executable instructions stored thereon that, when executed by the processor, cause the processor to constrain the end effector to a region defined by a subject's posterior tympanotomy.

Alternatively or additionally, the memory has further computer-executable instructions stored thereon that, when executed by the processor, cause the processor to constrain the end effector to an about 3 mm×3 mm×3 mm region.

Alternatively or additionally, the memory has further computer-executable instructions stored thereon that, when executed by the processor, cause the processor to control a position and an orientation of the robotic tool.

Alternatively or additionally, the memory has further computer-executable instructions stored thereon that, when executed by the processor, cause the processor to filter motions applied by a user to a user interface of the robotic system.

Alternatively or additionally, the memory has further computer-executable instructions stored thereon that, when executed by the processor, cause the processor to provide a visualization of cochlear insertion.

Alternatively or additionally, the memory has further computer-executable instructions stored thereon that, when executed by the processor, cause the processor to provide an alert in response to trauma.

Alternatively or additionally, the memory has further computer-executable instructions stored thereon that, when executed by the processor, cause the processor to control the robotic tool in response to commands received at the user interface. The user interface and the controller are operably coupled by a network.

Alternatively or additionally, the robotic tool is configured for attachment to a base. The base is an operating room bed.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Uke reference numerals designate corresponding parts throughout the several views.

FIG. 3A is a representation of the operating room (OR) showing the MTCI system in relation to a patient and surgical staff. FIG. 3B is a schematic (top view) of the OR showing attachment of the MTCI system to the OR bed in the right and left cochlea configurations. FIG. 3C is a schematic illustrating the kinematic arrangement of the MTCI system of FIGS. 3A and 3B. FIG. 3D illustrates the end effector of the of the MTCI system of FIGS. 3A and 3B.

DETAILED DESCRIPTION

Figure 1:
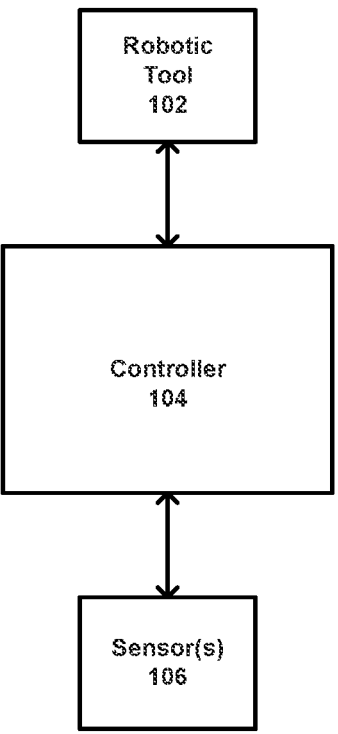
FIG. 1 is a block diagram of a robotic system for cochlear implant electrode array insertion according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "about" or "approximately" when referring to a measurable value such as an amount, a percentage, and the like, is meant to encompass variations of ±20%, ±10%, ±5%, or ±1% from the measurable value.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

Described herein is a robotic system for cochlear implant electrode array insertion that is configured to imitate the motion of a human hand. Such a robotic system can improve quality metrics such as insertion forces, acceleration, intracochlear electrode position, and/or intracochlear damage as compared to manual surgical procedures.

As described above, a low percentage of eligible patients undergo CI procedures, which is due, at least in part, to potential for residual hearing loss as a result of the procedure. There is therefore a need to improve the CI surgical procedures. For example, more recent efforts have focused on design modifications of the electrode carriers to improve hearing preservation (HP) rates. Clinical studies have confirmed that these changes have in fact resulted in improved preservation rates; however, many patients still lose substantial levels of RH following surgery. In particular, cochlear implant electrode array insertion is currently performed manually by the surgeon and the literature suggests that the small scale and the delicate nature of the cochlea will likely benefit from an automated process eliminating the surgeon's tremor, lowering the insertion speed, and improving the consistency of the insertion rate. Previously, several groups have proposed to utilize a robot for cochlear implantation. The vast majority of designs propose to use the robot to drill the surgical approach through the mastoid and facial recess. While this has been shown possible, difficult and cumbersome registration processes typically prolong surgical times beyond an acceptable level. Also, the actual electrode insertion is then further complicated by the small diameter of the resulting bony tunnel leading into the middle ear and subsequently the cochlea.

Alternatively, use of the robot has been proposed for electrode insertion only. This would mean that the surgeon will still need to furnish a standard CI approach including a mastoidectomy and facial recess before the robot can undertake the electrode insertion. One group has demonstrated that by using a relatively simple robotic design, the electrode can be advanced without manual assistance. However, this simple robotic design does not provide the degrees of freedom that the human hand allows, thus minimizing the robot's ability to modify insertion parameters such as pitch, rotation, and yaw during electrode advancement. This lack of dexterity may cause further unwanted intracochlear damage and consequently hearing loss, and thus lack of adoption by CI surgeons.

The robotic system for cochlear implant electrode array insertion described herein addresses one or more of the above deficiencies. The robotic system described herein is lightweight and compact, and it can perform CI after the approach and cochlear opening have been performed manually. The robotic system described herein provides superhuman attenuation of hand tremor, smooth insertion, and improved positioning resolution. Moreover, the robotic system described herein maintains critical aspects of the user's (e.g., surgeon's) experience while maintaining full dexterity of the user's hand but at submillimeter scale within a compact superstructure so as to not obscure vision through a dissecting microscope.

Referring now to FIG. 1, a robotic system for cochlear implantation (CI) is shown. The system includes a robotic tool 102 configured to hold a cochlear implant electrode array and a controller 104. This disclosure contemplates that the robotic tool 102 can be configured for attachment to a base such as an operating room (OR) bed. It should be understood that an OR bed is provided only as an example base. The robotic tool 102 can therefore be attached to/detached from the base using a coupling mechanism prior to the surgical procedure. Additionally, the robotic tool 102 can be configured to perform CI on either side (i.e., right or left side) of a subject, for example, by attaching the robotic tool 102 to the appropriate side of the OR bed. The controller 104 is operably coupled to the robotic tool 102. The robotic tool 102 and the controller 104 can be coupled by one or more communication links. This disclosure contemplates the communication links are any suitable communication link. For example, a communication link may be implemented by any medium that facilitates data exchange including, but not limited to, wired, wireless and optical links. Example communication links include, but are not limited to, a local area network (LAN), a wireless local area network (WLAN), a wide area network (WAN), a metropolitan area network (MAN), Ethernet, the Internet, or any other wired or wireless link such as WiFi, WiMax, 3G, 4G, or 5G. Example communication links also include wired, wireless, or optical links that facilitate exchange of analog and/or digital electrical signals where the transmitter or receiver is using a proprietary signal type and hardware has specialized drivers to receive the information. The controller 104 includes a processor and a memory. For example, the controller 104 can include at least the elements enclosed by dashed line 202 shown in FIG. 2.

The controller 104 can be configured to generate and transmit control signals to the robotic tool 102. The control signals are configured to drive the robotic tool 102 (e.g., driving one or more kinematic elements described below).

The controller 104 is configured to control the robotic tool 102 with the degrees of freedom comparable to a human hand. The robotic system provides for greater control over electrode advancement during the CI procedure as compared to conventional manual and proposed automated CI procedures. In some implementations, the degrees of freedom of a human hand include pitch, roll, and/or yaw. In some implementations, the controller 104 is configured to control the robotic tool 102 with at least three degrees of freedom (e.g., roll, pitch, and yaw). In some implementations, the controller 104 is configured to control the robotic tool 102 with at least six degrees of freedom (e.g., forward/back, up/down, left/right, roll, pitch, and yaw). In some implementations, the controller 104 is configured to control the robotic tool 102 with more than six degrees of freedom. For example, the human hand has twenty seven degrees of freedom due to the various bones in the fingers, thumb, and wrist. It should be understood that the robotic tool 102 can be designed to achieve various degrees of freedom comparable to the human hand.

Alternatively or additionally, the system optionally includes a sensor 106 operably coupled to the controller 104. The sensor 106 and the controller 104 can be coupled by one or more communication links. As described above, this disclosure contemplates the communication links are any suitable communication link including, but not limited to, wired, wireless and optical links. The sensor 106 is configured to detect a surgical procedure quality metric. Quality metrics can include, but are not limited to, insertion forces, acceleration, intracochlear electrode position, and/or intracochlear damage. For example, the sensor 106 can be a force sensor, a pressure sensor, an accelerometer, or an inertial sensor. It should be understood that force sensors, pressure sensors, accelerometers, and inertial sensors are only provided as examples. This disclosure contemplates that sensor 106 can be a sensor of a different type. Additionally, it should be understood that the system can include more than one sensor 106. Additionally, the sensors can be of the same type or different types. Optionally, the controller 104 can be further configured to receive a feedback signal from the sensor 106, and control the robotic tool 102 in response to the feedback signal.

As described above, the robotic tool 102 can be controlled with the degrees of freedom (DOF) of a human hand. This can be accomplished using kinematic elements. As used herein, a kinematic element is a component of the robotic tool 102 which moves relative to another component of the robotic tool 102. For example, the robotic tool 102 can include a plurality of kinematic elements (see e.g., joints $Z_{1-6}$ in FIG. 3C). The kinematic elements can include a prismatic joint. A prismatic joint (sometimes referred to as a "slider") is configured to provide linear movement (e.g., up to two DOF) between two bodies. Alternatively or additionally, the kinematic elements can include a revolute joint (sometimes referred to as a "pin joint" or "hinge joint"). A revolute joint is configured to allow for rotation (e.g., one DOF) of a body about an axis. Alternatively or additionally, the kinematic elements can include combinations of prismatic and revolute joints. It should be understood that prismatic and revolute joints are provided only as example kinematic elements. This disclosure contemplates using other types of kinematic elements to facilitate robotic motion. For example, in one implementation, the kinematic elements can include one or more kinematic elements (see e.g., joints $Z_{1-4}$ in FIG. 3C) configured for gross positioning and rotation, one or more kinematic elements (see e.g., joints $Z_{5-6}$ in FIG. 3C) configured for fine rotation, and one or more kinematic elements (see e.g., joint $Z_7$ in FIG. 3C) configured for retracting an end effector of the robotic tool 102. It should be understood that the number and/or arrangement of kinematic elements in the example above are provided only as an example. This disclosure contemplates providing a robotic tool with different numbers and/or arrangement of kinematic elements.

Alternatively or additionally, the robotic tool 102 includes an end effector. The end effector of the robotic tool 102 is sized and shaped to fit into a subject's facial recess, which has a maximum anterior posterior diameter of about 3 mm. Thus, as described herein, the end effector can be sized, shaped, and/or controlled to fit within an about 3 millimeter (mm)×3 mm×3 mm region. It should be understood that the area outside the facial recess is considerably larger. In order to provide the degrees of freedom described herein, dimensions of the robotic tool 102 configured to be positioned outside the facial recess should not exceed about 6-8 mm. An example end effector 350 is shown in FIG. 3D. It should be understood that the size, shape, and design of the end effector in FIG. 3D are provided only as an example. The end effector is the mechanical interface that releasably grips the cochlear implant electrode array (e.g., electrode 360 in FIG. 3D). Optionally, the end effector is tapered at its distal end. As described in the Examples below, the end effector is designed to fit in a cavity formed by a subject's posterior tympanotomy. Optionally, the end effector is sized, shaped, and/or controlled to fit within an about 3 mm×3 mm×3 mm region. Alternatively or additionally, the controller 104 can be configured to constrain the end effector to a region defined by the subject's posterior tympanotomy and/or a 3 mm×3 mm×3 mm region.

In some implementations, the controller 104 is configured to control a position and an orientation of the robotic tool 102. Optionally, the controller 104 can be configured to control the position and orientation of the robotic tool 102 according to an optimized trajectory. This disclosure contemplates that the optimized trajectory may be computed according to techniques known in the art, for example by a temporal bone simulator or other means. For example, the controller 104 sends commands to control (e.g., actuate) movement (e.g., position and rotation) of the robotic tool 102. This can be accomplished as described in the Examples below. For example, if the frame of the robotic tool 102 is denoted {T} and the frame of the base (i.e., structure to which the robotic tool 102 is attached) is denoted by {B}, then the controller 104 controls to the robotic tool 102 using a 3-D position vector, $$ {}^T_B P, $$

and 3-D rotation matrix, $$ {}^T_B R. $$

Optionally, the controller 104 is configured to control the robotic tool in response to commands received at a user interface (e.g., user interface 304 in FIG. 3B) of the controller 104. This disclosure contemplates that the user interface can a hardware interfaced configured to receive the user's hand such that the user can manipulate the robotic tool 102. An example user interface is the Phantom Omni haptic device developed by SensAble Technologies, Inc. of Wilmington, MA. The Phantom Omni haptic device is a portable 6 DOF haptic device known in the art. It should be understood that the Phantom Omni haptic device is provided only as an example. This disclosure contemplates using other user interfaces for controlling the robotic tool 102. The user interface and controller 104 are coupled by one or more communication links such as wired, wireless and optical links. Optionally, the user interface is remote with respect to the robotic tool 102, for example a telemedicine application. In this implementation, the user interface and the controller 104 are operably coupled by a network (e.g., a LAN, WLAN, WAN, MAN, Ethernet, or Internet). Alternatively or additionally, the controller 104 receives a feedback signal from the sensor 106 (e.g., force, pressure, acceleration, position, orientation, or other feedback signal), which can be used for controlling the robotic tool 102. Alternatively or additionally, the controller can receive radiological information and/or electrocochleography based feedback, which can be used for controlling the robotic tool 102. Electrocochleography (ECochG) is a technique known in the art where electrical potentials generated in the inner ear and auditory nerve in response to stimulation (e.g., sound) are recorded by an electrode. Such electrode is typically placed in the subject's ear canal or tympanic membrane. It should be understood that the electrode placement location is provided only as an example and that the electrode may be placed in any location where ECochG signals can be recorded.

In some implementations, the controller 104 is configured to filter motions applied by a user to a user interface of the robotic system. This disclosure contemplates that the user may apply forces (e.g., voluntary or involuntary movements, tremors, etc.) to the user interface, which may be transferred to the robotic tool 102. The controller 104 can attenuate such forces applied by the user that are transferred to the robotic tool 102.

In some implementations, the controller 104 is configured to provide a visualization of cochlear insertion. This disclosure contemplates providing a visualization on a display of the controller 104. As described above, the controller 104 controls to the robotic tool 102 using a 3-D position vector, $$_B^T P,$$

and 3-D rotation matrix, $$_B^T R,$$

and the controller 104 receives a feedback signal from the sensor 106. Thus, the controller 104 can analyze the feedback signal(s) and provide visualizations of cochlear insertion. Alternatively or additionally, the visualizations may be a stereoscopic visualization acquired by a dissection microscope.

In some implementations, the controller 104 is configured to provide an alert in response to trauma. This disclosure contemplates providing a visualization on a display of the controller 104. As described above, the controller 104 controls to the robotic tool 102 using a 3-D position vector, $$_B^T P,$$

and 3-D rotation matrix, $$_B^T R,$$

and the controller 104 receives a feedback signal from the sensor 106. Thus, the controller 104 can analyze the feedback signal(s) and provide visualizations of the alert, which may be an audio, video, or tactile alert.

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
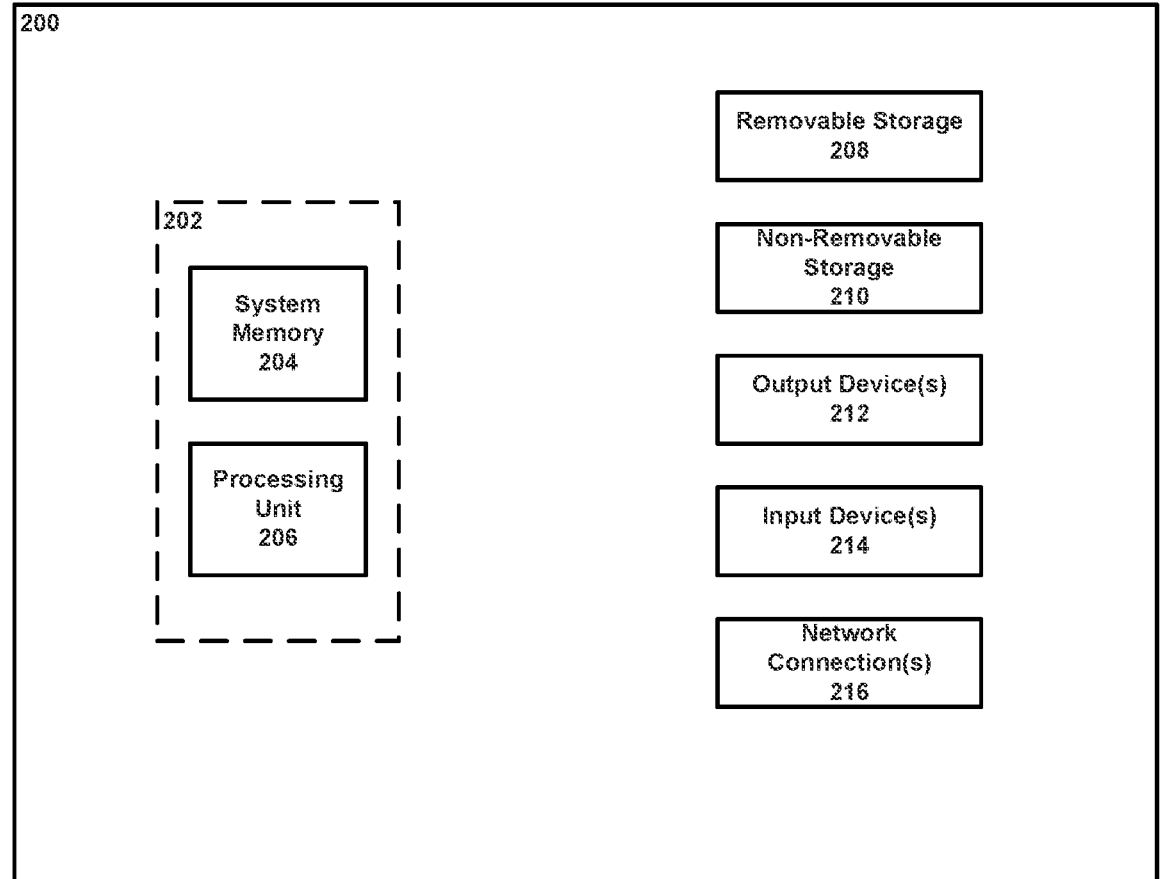
FIG. 2 is an example computing device.

Referring to FIG. 2, an example computing device 200 upon which the methods described herein may be implemented is illustrated. It should be understood that the example computing device 200 is only one example of a suitable computing environment upon which the methods described herein may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), nonvolatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 3A:
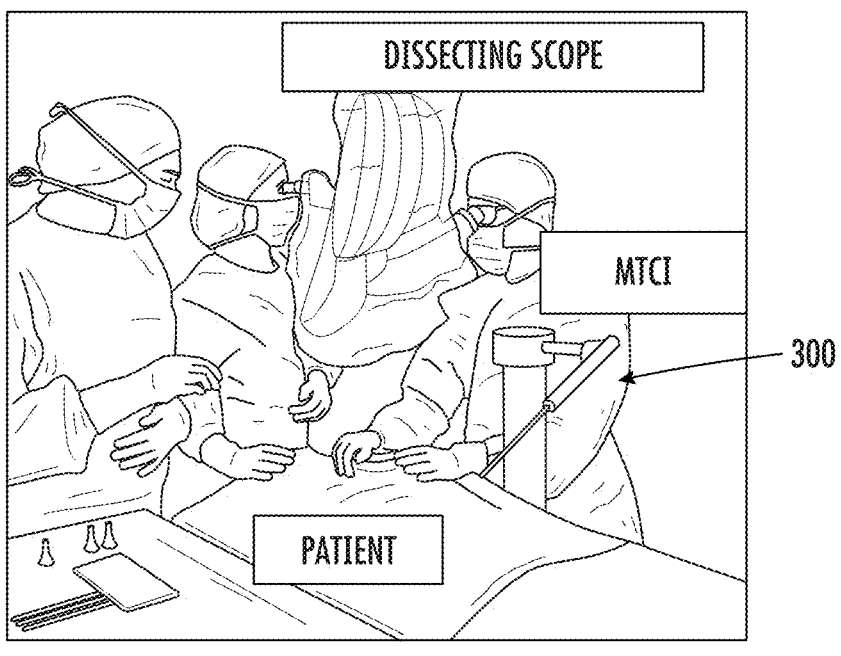
FIGS. 3A-3D illustrate an example robotic system for cochlear implant electrode array insertion (also referred to herein as Minimally Traumatic Cochlear Implantation (MTCI) system) according to one implementation described herein.
Figure 3B:
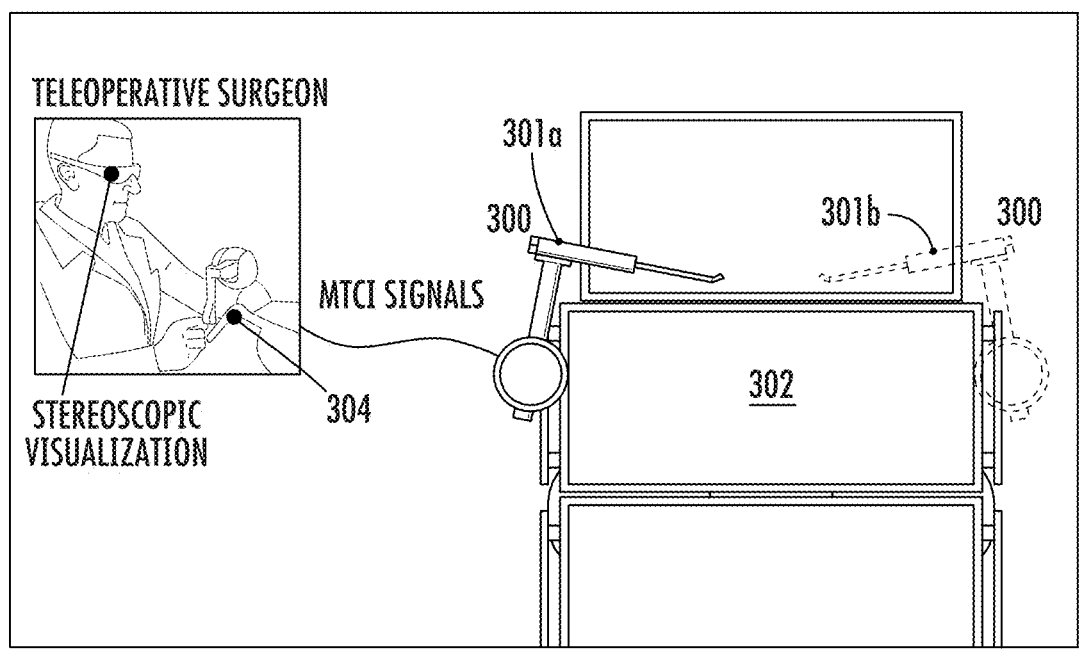
Figure 3C:
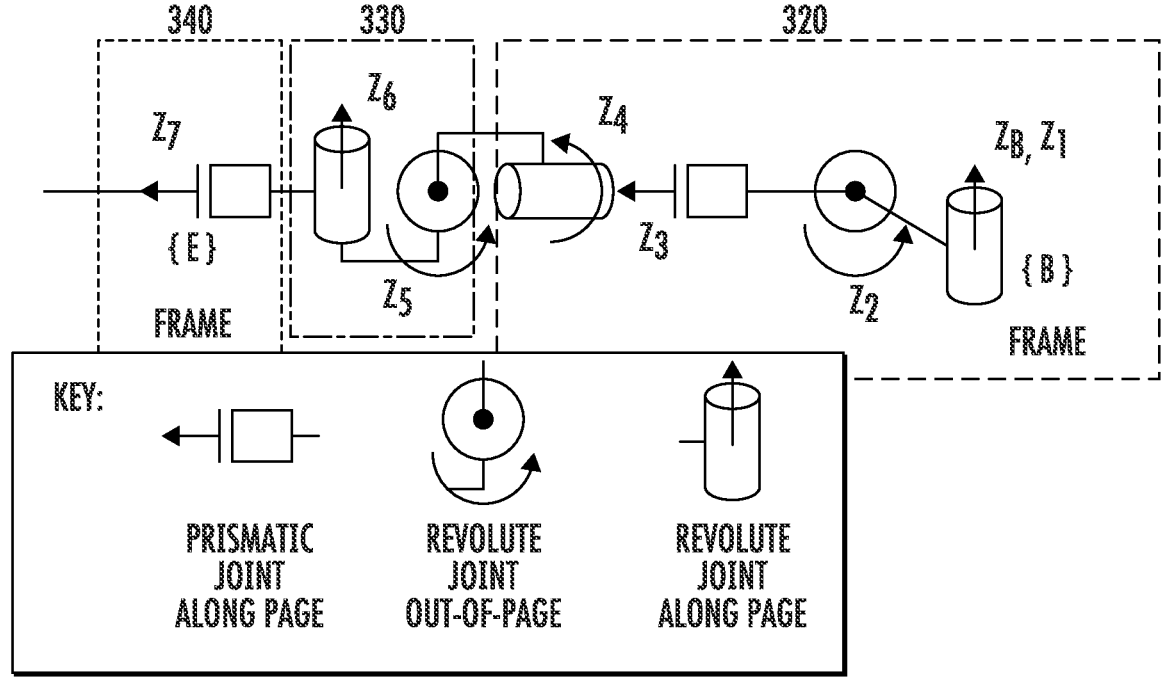
Figure 3D:
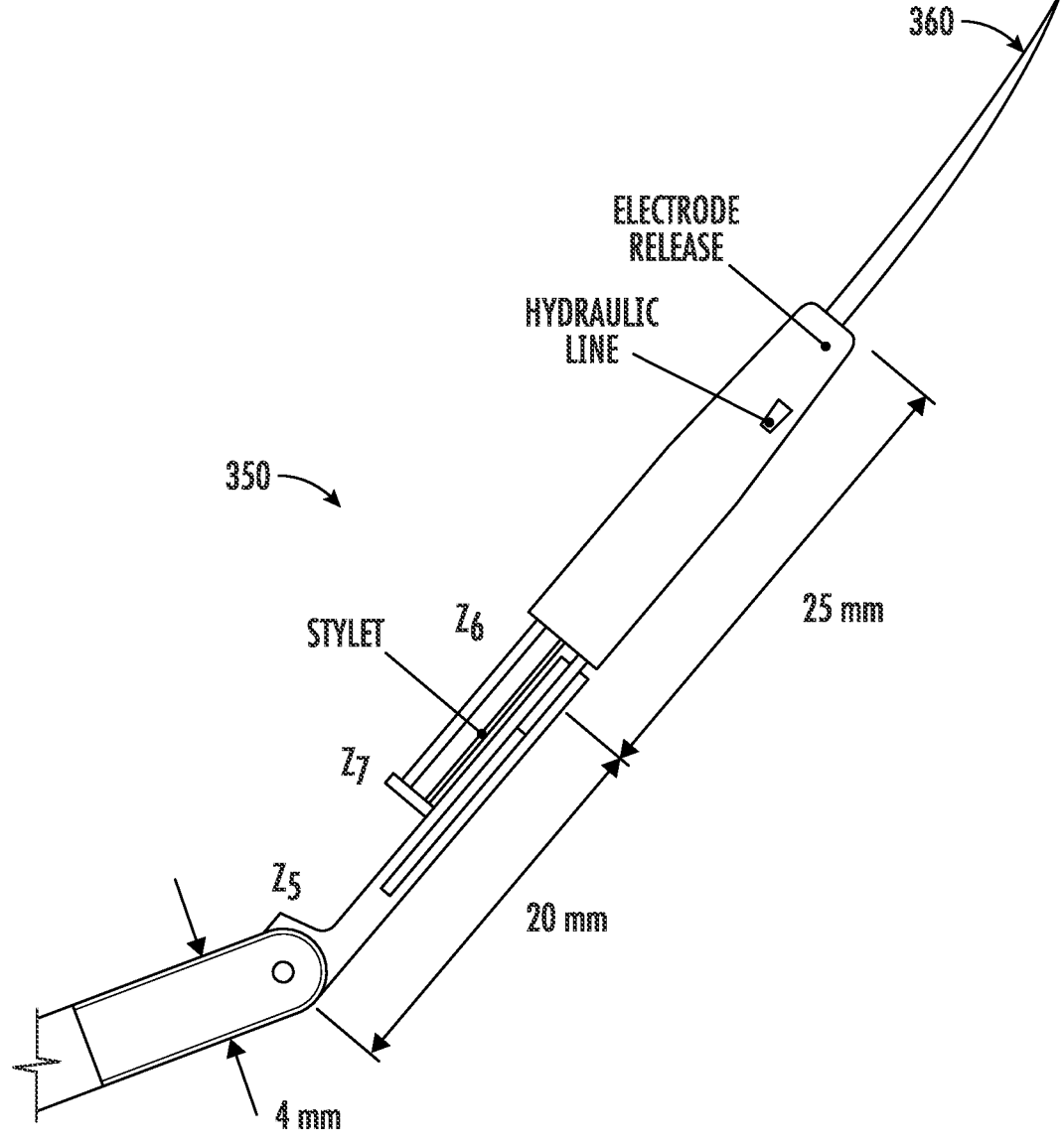

Referring now to FIGS. 3A-3D, an example robotic system for cochlear implant electrode array insertion (also referred to herein as Minimally Traumatic Cochlear Implantation (MTCI) system) is described below. FIG. 3A is a representation of the operating room (OR) showing the MTCI system 300 in relation to a patient and surgical staff. FIG. 3B is a schematic (top view) of the OR showing attachment of the MTCI system 300 to the OR bed 302 in the right cochlea configuration (labeled 301*a*) and left cochlea configuration (labeled 301*b*). The surgeon's user interface 304, which in operable communication with a controller, is also shown in FIG. 3B. FIG. 3C is a schematic illustrating the kinematic arrangement of the MTCI system of FIGS. 3A and 38. The MTCI system is separated into gross positioning and rotation axes 320 (joints $Z_{1-4}$, which are observable in FIGS. 3A and 3B) and fine rotation axes 330 (joints $Z_{5-6}$) and stylet retraction axis 340 (joint $Z_7$). The fine rotation and stylet retraction axes 330, 340 are designed to fit within the confines of the cavity formed by the posterior tympanotomy. FIG. 3D illustrates the end effector 350 of the of the MTCI system of FIGS. 3A and 38, including the fine rotation axes (joints $Z_{5-6}$) and stylet retraction axis (joint $Z_7$) shown in FIG. 3C. The end effector 350 grips the electrode 360, which will be implanted into a patient.

Initially, some standard robotics definitions are reviewed to appropriately introduce the MTCI system. Individual objects in a robotic system are assigned frames, which are simply coordinate systems affixed to the object, with are defined by their position and orientation. The typical objective for a robotic system is to manipulate an object of interest—in this example case the CI electrode array (see electrode 360 in FIG. 3D). Accordingly, a toolframe, denoted {T}, is assigned to the base of the CI array. The component that grips the array is termed the end effector (see end effector 350 in FIG. 3D), denoted frame {E} (shown in FIG. 3C). For purposes of manipulating a CI electrode array, the objective is to control the position and rotation of the tool, denoted by the three dimensional (3-D) position vector, $$^T_B P = [P_x, P_y, P_z],$$

and 3-D rotation matrix, $$_B^T R,$$

relative to the base frame {B} (shown in FIG. 3C), which is a frame assigned to a fixed body; in the problem herein, the base frame is the operating room (OR) bed (see OR bed 302 in FIG. 3B). A robotic system such as the MTCI system 300 designed for surgeon-controlled insertion of a CI electrode array controls the position vector $$_B^T P$$

and 3-D rotation matrix $$_B^T R,$$

relative to the base at all points in time, as dictated by the surgeon through their controls, for example using a user interface (see surgeon's user interface in FIG. 3B).

The requirements of sub-millimeter positioning accuracy and sub-degree orientation accuracy, whilst scaling motions, filtering tremors, and following instructions from a user interface, are fairly routine for off-the-shelf robotics systems. The MTCI system described herein is different from off-the-shelf robotics systems, and therefore significantly impacts CI, because the MTCI system can provide fully dexterous manipulation of the electrode (3 positional degrees of freedom (DOF) and 3 rotational DOFs) with an end effector that fits in the small, millimeterspace of the surgically created recess between the facial nerve and its chorda tympani branch. The MTCI system provides a compact robotic system that mounts to an OR bed, grips standard CI electrode array, and provides the full insertion dexterity of the surgeon hand, while being remotely controlled from a console that both filters out tremors and provides visualization of insertion.

The MTCI system of FIGS. 3A-3D is composed of three main elements: 1) kinematic elements for continually positioning and orienting the electrode (see FIG. 3C), 2) electrode insertion end effector (see FIG. 3D), and 3) a surgeon control interface for visualization (continuous position, orientation, and insertion control) (see FIG. 3B). The robotic portion (elements 1+2) are designed to be docked to the standard OR bed during electrode insertion and undocked when not being used (see FIG. 3B). A single MTCI system can be used for either a right or left sided surgery (see FIG. 3B, right and left cochlea configurations 301*a*, 301*b*).

Kinematic elements: The kinematic (see FIG. 3C) arrangement of the MTCI system 300 uses the 'Stanford' manipulator architecture, which provides 6 degree of freedom (DOF) (e.g., 3 positioning DOF and 3 orientation DOF) by the coordination of 6 joints (labeled $Z_{1-6}$ in FIG. 3C). This 'Stanford' manipulator architecture is beneficial for C insertion because the gross movement prismatic joint allows the surgeon a controllable insertion of the end effector into the cavity formed by the posterior tympanotomy, without robot links interfering with or obstructing the view of the dissecting scope.

End effector: The end effector (see end effector 350 in FIG. 3D) is composed of a mechanical interface that releasably mates with the base of the electrode (see electrode 360 in FIG. 3D) and can be used with or without a stylet, depending on the preferred brand of electrode to be used. The kinematic arrangement (joints $Z_{1-6}$ in FIG. 3C), enable the end effector to be continuously placed in any position and orientation, enabling a surgeon to facilely change the electrode approach as it is inserted into the cochlea. The stylet insertion depth is controlled independently of end effector position and rotation control.

The end effector must fit within the cavity formed by the posterior tympanotomy, and is thus constrained to a size envelope of approximately 3 mm×3 mm×3 mm. Consequently, the end effector tapers at the distal end and the electrode release and stylet drive ($Z_7$) actuators are driven by microscale hydraulic actuators, which permit the work from larger hydraulic drives near the base of the robot to be transferred to the end effector through sub-mm tubing, such as is the design with many commercial micromanipulators (e.g. Newport MX530). The MTCI system approach described in this example differs from that of the Hannover group (Lenarz T, Dalkowski K. Cochlear implantation: the Hannover guideline. Tuttlingen: Endo-Press; 2006). In particular, the piezoelectric motors used by the Hannover group have nanometer (nm) scale precision, which is unnecessarily precise, but a stroke length on the order of 1 millimeter (mm), which does not permit full electrode insertion. To compensate for the small stroke length, the Hannover group's system operates in a stepping mode, which can result in stage vibration and an audible buzz. In contrast, the 'Stanford' manipulator architecture is used with the MTCI system described herein. For example, in this configuration, joints $Z_{5-6}$ in FIG. 3C are cable driven to permit relatively large revolute joint torques from stronger motors placed far from the end effector.

Surgeon control interface: The surgeon control interface (see interface 304 in FIG. 3B) receives the surgeon commands via a master interface (e.g., Phantom Omni haptic device), coordinates all robot axis motions, filters tremors received at the master interface, provides stereoscopic visual information from a dissecting scope, and provides audio/visual alerts of trauma. Optionally, the MTCI system 300 can be operated remotely (i.e. teleoperation), which allows for digitally scaling the relationship between surgeon input at the master interface and motion at the end effector, providing movement precision that exceeds human capabilities. The interface provides a visualization of the process of insertion.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A robotic system for cochlear implantation (CI), comprising:
   a robotic tool configured to hold a cochlear implant electrode array; and
   a controller operably coupled to the robotic tool, the controller comprising a processor and a memory operably coupled to the processor, the memory having computer-executable instructions stored thereon that, when executed by the processor, cause the processor to control the robotic tool with a plurality of degrees of freedom comparable to a human hand and cause the processor to constrain an end effector of the robotic tool to a region with a largest dimension of 3 mm or less.

2. The robotic system of claim 1, wherein the plurality of degrees of freedom comparable to the human hand comprise at least one of pitch, roll, or yaw.

3. The robotic system of claim 1, further comprising a sensor operably coupled to the controller, wherein the sensor is configured to detect a surgical procedure quality metric.

4. The robotic system of claim 3, wherein the sensor is a force sensor, a pressure sensor, an accelerometer, an inertial sensor, or an electrode.

5. The robotic system of claim 3, wherein the memory has further computer-executable instructions stored thereon that, when executed by the processor, cause the processor to receive a feedback signal from the sensor, and control the robotic tool in response to the feedback signal.

6. The robotic system of claim 1, wherein the robotic tool comprises a plurality of kinematic elements.

7. The robotic system of claim 6, wherein the kinematic elements comprise a prismatic joint, a revolute joint, or combinations thereof.

8. The robotic system of claim 6, wherein the kinematic elements comprise one or more kinematic elements configured for gross positioning and rotation, one or more kinematic elements configured for fine rotation, and one or more kinematic elements configured for retracting an end effector of the robotic tool.

9. The robotic system of claim 1, wherein the end effector is tapered at a distal end.

10. The robotic system of claim 1, wherein the memory has further computer-executable instructions stored thereon that, when executed by the processor, cause the processor to constrain the end effector to a region defined by a subject's posterior tympanotomy.

11. The robotic system of claim 1, wherein the memory has further computer-executable instructions stored thereon that, when executed by the processor, cause the processor to constrain the end effector to an about 3 mm×3 mm×3 mm region.

12. The robotic system of claim 1, wherein the memory has further computer-executable instructions stored thereon that, when executed by the processor, cause the processor to control a position and an orientation of the robotic tool.

13. The robotic system of claim 1, wherein the memory has further computer-executable instructions stored thereon that, when executed by the processor, cause the processor to filter motions applied to a user interface of the robotic system.

14. The robotic system of claim 1, wherein the memory has further computer-executable instructions stored thereon that, when executed by the processor, cause the processor to provide a visualization of cochlear insertion.

15. The robotic system of claim 1, wherein the memory has further computer-executable instructions stored thereon that, when executed by the processor, cause the processor to provide an alert in response to trauma.

16. The robotic system of claim 1, further comprising a user interface operably coupled to the controller, wherein the memory has further computer-executable instructions stored thereon that, when executed by the processor, cause the processor to control the robotic tool in response to commands received at the user interface.

17. The robotic system of claim 16, wherein the user interface and the controller are operably coupled by a network.

18. The robotic system of claim 1, wherein the robotic tool is configured for attachment to a base.

19. The robotic system of claim 18, wherein the base is an operating room bed.

* * * * *